United States Patent [19]

Volkwein et al.

[11] 4,306,103

[45] Dec. 15, 1981

[54] PROCESS FOR THE MANUFACTURE OF 1,3,5-TRICHLOROBENZENE

[75] Inventors: Gert Volkwein, Kelkheim; Konrad Baessler, Frankfurt am Main; Hans Wolfram, Kelkheim, all of Fed. Rep. of Germany

[73] Assignee: Hoechst Aktiengesellschaft, Frankfurt, Fed. Rep. of Germany

[21] Appl. No.: 150,569

[22] Filed: May 16, 1980

[30] Foreign Application Priority Data

May 18, 1979 [DE] Fed. Rep. of Germany ....... 2920173

[51] Int. Cl.$^3$ .............................................. C07C 25/02
[52] U.S. Cl. .................................... 570/201; 570/207
[58] Field of Search ........................ 570/201, 207, 182

[56] References Cited

U.S. PATENT DOCUMENTS

2,354,813  8/1944  Jenkins ............................... 570/201
3,256,351  6/1966  Leib .................................... 570/201

FOREIGN PATENT DOCUMENTS

1503153 10/1967 France .
 987000  3/1965 United Kingdom .
1158875  7/1969 United Kingdom .

OTHER PUBLICATIONS

Houben–Weyl, vol. 3, (1962), pp. 750–751.

Primary Examiner—Curtis R. Davis
Attorney, Agent, or Firm—Curtis, Morris & Safford

[57] ABSTRACT

1,3,5-trichlorobenzene is manufactured by treating 5-chloro-1,3-dinitrobenzene and/or 3,5-dichloronitrobenzene with chlorine, at a temperature from about 200° to 270° C., preferably from about 230° to 250° C. The resulting process product is an intermediate, for example in plant protection.

5 Claims, No Drawings

PROCESS FOR THE MANUFACTURE OF 1,3,5-TRICHLOROBENZENE 1,3,5-Trichlorobenzene is a valuable intermediate in various fields, such as in plant protection, for example to manufacture the plant protecting agent trichlorotrinitrobenzene.

1,3,5-Trichlorobenzene cannot be obtained by direct chlorination of benzene and must hence be synthesized in different way.

For example, it has been proposed to convert 1,2,4-trichlorobenzene into 1,3,5-trichlorobenzene by isomerization with Friedel-Crafts catalysts and cocatalysts such as magnesium sulfate, methanol or water [U.S. Pat. No. 3,866,829; Z. obsc. Chim. 34 (1964) 1,237; German Pat. No. 947,304 (1956)].

However, all of these processes are unsatisfactory because of a relatively low conversion and the considerable expenditure of time and money on fractionation necessary.

Other methods of synthesis involve several reaction steps that are rather complicated such as diazotization and concentration, for example of 2,4,6-trichloroaniline [J. of Chem. Soc. (London) (1947), 173] or of 3,5-dichloroaniline which is difficult to obtain [Rec. Trav. Chim. d. Pays-Bas 37 (1918), 198].

It has moreover been proposed [Houben-Weyl vol. 3 (1962), page 750] to replace nitro groups by chlorine, with of elementary chlorine ("denitrating chlorination") at elevated temperature, in the absence of catalysts inducing chlorination of the nucleus. Either one or two nitro groups may be replaced in this procedure; a shifting of the substituents does not take place. For example, a mixture consisting of 68% of m-dichlorobenzene and of 25% of m-chloronitrobenzene can be obtained from m-dinitrobenzene, at 220° C., in a 79% yield (BIOS, Final Rep. 986 I, 151). The reaction proceeds in analogous manner with o-dinitrobenzene and with p-dinitrobenzene, i.e., only one nitro group is replaced and p-chloronitrobenzene is obtained [Ber. deutsch. Chem. Ges. 24 (1891), 3749]. When running the reaction with 2,4-dinitrotoluene, likewise only one nitro group is replaced and chloronitrobenzoic acid is obtained with simultaneous oxidation of the $CH_3$ group [Zh. Org. Khim. 9 (1973) 4,762].

The problem of improving the known processes for the manufacture of 1,3,5-trichlorobenzene or of providing a novel improved process has been solved by the present invention in simple and satisfactory manner by treating 5-chloro-1,3-dinitrobenzene and/or 3,5-dichloronitrobenzene at a temperature from approximately 200° to 270° C., preferably from approximately 220° to 250° C., with chlorine.

In this treatment with chlorine, the nitro groups of both starting materials are completely replaced by chlorine in smooth manner. This reaction is hereinafter referred to as denitrating chlorination.

This smooth course of the denitrating chlorination was extremely surprising in view of the relevant state of the art, for in the chlorination of dinitrobenzenes and of 2,4-dinitrotoluene only one nitro group is completely replaced by chlorine, while the second nitro group is reported to be replaced in incomplete manner, when the benzene nucleus has been substituted by chlorine (BIOS, loc. cit.: m-Dinitrobenzene→Mixture of m-dichlorobenzene+m-chloronitrobenzene; Ber. d. deutsch. chem. Ges. 24 loc. cit.: o-dinitrobenzene→mixture of o-dichlorobenzene+o-chloronitrobenzene) or to be not at all replaced (Berichte der deutschen chemischen Gesellschaft 24 loc. cit.: p-Dinitrobenzene→p-chloronitrobenzene; Zh. Org. Chim. 9 loc. cit.: 2,4-dinitrotoluene→chloronitrobenzoic acid).

The process of the invention is carried out suitably in the following manner: Chlorine is introduced into a receptacle containing a suitable reactant free of catalysts which induce chlorination of the nucleus especially iron. For example 5-chloro-1,3-dinitrobenzene or 3,5-dichloronitrobenzene or any mixture of these compounds, are heated at a temperature of from approximately 200° to 270° C., preferably from approximately 230° to 250° C., until the trichlorobenzene obtained is refluxing. Preferably the molar quantity of chlorine must be equal to at least half the number of the nitro groups per molecule of the starting compound. For example, when 1 mol of 5-chloro-1,3-dinitrobenzene is used as starting compound, chlorination must be run using at least one mol of chlorine when using as the starting product 3,5-dichloronitrobenzene. When starting from a mixture of both of the above-mentioned compounds, the minimum quantity of chlorine has to range between 0.5 mol and one mol of chlorine. When chlorine is charged at a constant rate, the trichlorobenzene obtained is practically free from nitro product; it is distilled off over a connected column, while the product to be denitrated passes into the sump so that the quantity of product in the sump remains constant. This continuous method permits the use of relatively small reaction vessels and yields 1,3,5-trichlorobenzene, dependent on the length of the column used, in a purity greater than 99%, in a yield of approximately 95% of the theory. This continuous method is therefore preferred over discontinuous or batch operation. The reaction product obtained has simply to be washed neutral, and then dried.

In a further preferred embodiment of the process according to the invention, the starting product 5-chloro-1,3-dinitrobenzene is used in admixture with m-dinitrobenzene. This embodiment is preferred, for the mixture of 5-chloro-1,3-dinitrobenzene and m-dinitrobenzene is obtained in the (incomplete) chlorination of the nucleus of m-dinitrobenzene; hence, this mixture can be used directly for the reaction according to the invention, upon appropriate purification (separation of the catalyst inducing a chlorination in the nucleus). In principle the mixture can have any composition, depending on on the degree of chlorination of the m-dinitrobenzene. However, the portion of 5-chloro-1,3-dinitrobenzene should preferably amount to at least 20 weight %, especially to at least approximately 40 weight %. When chlorinating with a quantity of chlorine sufficient to effect a complete replacement of all nitro groups, there is formed a mixture of 1,3,5-trichlorobenzene and of m-dichlorobenzene. This complete replacement of the nitro groups, even of those of m-dinitrobenzene, by chlorine, was surprising in view of what has been reported in BIOS loc. cit. This complete replacement is perhaps due to the fact that the replacement of the nitro groups of 5-chloro-1,3-dinitrobenzene has an inducing effect on the complete replacement of the nitro groups of m-dinitrobenzene.

The denitrating chlorination of 5-chloro-1,3-dinitrobenzene, in admixture with m-dinitrobenzene as well as the treatment with chlorine of 5-chloro-1,3-dinitrobenzene alone or in admixture with 3,5-dichloronitrobenzene according to the invention, can be run continuously or discontinuously, the continuous mode of operating being preferred. The different boiling points of 1,3,5-trichlorobenzene and m-dichlorobenzene do not unfavorably affect the continuous process according to the invention. On the contrary, a separation of 1,3,5-trichlorobenzene and of m-dichlorobenzene by way of distillation is even facilitated by these different boiling points.

The process according to the invention yields 1,3,5-trichlorobenzene and possibly even m-dichlorobenzene in economic, low-polluting manner, in a good to very good yield, even when performed on an industrial scale and it represents hence a considerable advancement of the art.

The following examples illustrate the present invention.

EXAMPLE 1

1,500 g of 3,5-dichloronitrobenzene are fed to a 2 liter flask equipped with gas introduction tube and on which is mounted a well-insulated vacuum jacket column provided with approximately 20 theoretical plates, a reflux partition and which is heated with a mushroom heating cap; the 3,5-dichloronitrobenzene is heated to 230° C. Chlorine is introduced at a rate of 12 liters/hour. After approximately 5 hours, the quantity of 1,3,5-trichlorobenzene formed is such that refluxing occurs in the fractionating column. The sump contains a crude product having a solidification point of approximately 54° C., which corresponds to a content of 1,3,5-trichlorobenzene of approximately 15%.

Next, 1,3,5-trichlorobenzene is withdrawn and 3,5-dichloronitrobenzene in the molten state is added at the same rate so that the quantity of product in the sump remains constant. When adding 150 g (about 110 cm$^3$) (80° C.) of 3,5-dichloronitrobenzene per hour, there are obtained approximately 140 g (105 cm$^3$, 80° C.) of 1,3,5-trichlorobenzene in a crude state, which is washed with water and with dilute sodium hydroxide solution and subsequently dried in the molten state at 100° C./50 mm. Per hour there are obtained 134 g (about 100 cm$^3$, 80° C.) of 1,3,5-trichlorobenzene, of a purity of 94.6% of the theory and having a solidification point of 62.4° C.

Gas chromatographic analysis:
0.2% of dichlorobenzene,
99.5% of 1,3,5-trichlorobenzene,
0.2% of 3,5-dichloronitrobenzene and
0.1% of several unknown substances.

EXAMPLE 2

1,200 g of a chlorination mixture consisting of 54% of m-dinitrobenzene and of 40% of 5-chloro-1,3-dinitrobenzene are placed into a 2 liter flask equipped with gas introduction tube and on which is mounted a well-insulated column having approximately 6 theoretical plates and a reflux partition (heatable) and which is heated by a mushroom heating cap; the chlorination mixture is heated to 230° C. Chlorine is introduced at a rate of 20 liters/hour. After about 8 hours low boiling products are to be found in the sump in an amount such that the reaction mixture starts to boil and that a reflux process is brought about in the fractionating column. The rate of introduction of chlorine is reduced to 15 liters/hour and the mixture of trichlorobenzene and of dichlorobenzene is withdrawn at the same rate at which the chlorination mixture is introduced so that the quantity of product contained in the sump is kept constant.

During the first 6 to 8 hours there are obtained products that contain from 80 to 60% of m-dichlorobenzene, for the content of the latter in the sump drops in the beginning to 2 to 3%, while the content of 1,3,5-trichlorobenzene is increased to 15 to 20%. Thereafter there are obtained constant conditions with a head temperature of approximately 170° C.

With a rate of introduction of chlorination mixture of 80 g (about 57 cm$^3$, 80° C.) per hour there are obtained per hour about 70 g (55 cm$^3$, 80° C.) of a mixture of 1,3,5-trichlorobenzene and of m-dichlorobenzene, in a crude state, which mixture is washed neutral with water and with dilute sodium hydroxide solution and dried subsequently in the molten state. Per hour there are obtained 66 g (about 50 cm$^3$, 50° C.) of a mixture of 1,3,5-trichlorobenzene and of m-dichlorobenzene, which corresponds to 82.5% of the weight of the starting material and to about 93% of the theoretical yield. The solidification point is 17.5° C.

Gas chromatographic analysis:
54% of m-dichlorobenzene,
0.3% of o-dichlorobenzene,
40% of 1,3,5-trichlorobenzene
3% of 1,2,4-trichlorobenzene,
0.3% of 1,2,3-trichlorobenzene,
0.2% of tetrachlorobenzenes,
2% of m-chloronitrobenzene and
0.2% of 3,5-dichloronitrobenzene.

1,3,5-Trichlorobenzene and m-dichlorobenzene are isolated in known manner by fractionating distillation.

What is claimed is:

1. A process for the manufacture of 1,3,5-trichlorobenzene, which comprises reacting chlorine with 5-chloro-1,3-dinitrobenzene, 3,5-dichloronitrobenzene or a mixture thereof, at a temperature from about 200° to 270° C., in the absence of a catalyst.

2. A process as claimed in claim 1, which comprises reacting at a temperature of from about 230° to 250° C.

3. A process as claimed in claim 1 or 2, which further comprises reacting chlorine with a mixture of 5-chloro-1,3-dinitrobenzene and m-dinitrobenzene.

4. A process as claimed in claim 1, which further comprises continuously introducing 5-chloro-1,3-dinitrobenzene, 3,5-dichloronitrobenzene, or a mixture thereof, and chlorine to the reaction at a constant rate and distilling off 1,3,5-trichlorobenzene.

5. A process as claimed in claim 4, which further comprises continuously introducing chlorine with a mixture of 5-chloro-1,3-dinitrobenzene and m-dinitrobenzene to the reaction at a constant rate and distilling off 1,3,5-trichlorobenzene and m-dichlorobenzene.

* * * * *